(12) United States Patent
Maggioni

(10) Patent No.: US 10,702,566 B2
(45) Date of Patent: Jul. 7, 2020

(54) MEDICAMENT FOR THE TREATMENT AND/OR PREVENTION OF ENDOMETRIOSIS

(71) Applicant: GIONAS S.R.L., Milan (IT)

(72) Inventor: Cristina Maggioni, Venice (IT)

(73) Assignee: GIONAS S.R.L., Milan (IT)

( * ) Notice: Subject to any disclaimer, the term of this patent is extended or adjusted under 35 U.S.C. 154(b) by 0 days.

(21) Appl. No.: 16/321,980

(22) PCT Filed: Jul. 31, 2017

(86) PCT No.: PCT/IB2017/054667
§ 371 (c)(1),
(2) Date: Jan. 30, 2019

(87) PCT Pub. No.: WO2018/025165
PCT Pub. Date: Feb. 8, 2018

(65) Prior Publication Data
US 2019/0167741 A1    Jun. 6, 2019

(30) Foreign Application Priority Data
Aug. 1, 2016  (IT) .................. 102016000080802

(51) Int. Cl.
  *A61K 36/23*  (2006.01)
  *A61K 36/24*  (2006.01)
  *A61P 15/00*  (2006.01)
  *A61K 9/00*   (2006.01)

(52) U.S. Cl.
  CPC .............. *A61K 36/23* (2013.01); *A61K 36/24* (2013.01); *A61P 15/00* (2018.01); *A61K 9/0053* (2013.01); *A61K 2236/33* (2013.01)

(58) Field of Classification Search
  None
  See application file for complete search history.

(56) References Cited

U.S. PATENT DOCUMENTS

| 7,402,325 B2 * | 7/2008 | Addington ............. | A61K 36/24 424/770 |
| 2006/0135443 A1 * | 6/2006 | Khodadoust ........... | A61K 31/56 514/26 |

OTHER PUBLICATIONS

Rezazad (Iranian Journal of Reproductive Medicine (May 2013), vol. 11, suppl. 2, pp. 70. Abstract No. P-95).*
Z Living article ("5 Ways to Treat Endometriosis Naturally" https://www.zliving.com/health/womens-health/5-ways-treat-endometriosis-naturally-21673/—Dec. 23, 2017).*
Anonymous, "ublich isoliert: natürlich Heilmittel für Endometriose", Feb. 1, 2013. XP055365966, Retrieved from the Internet: URL: http://ublichisoliert.blogspot.de/2013/02/naturliche-heilmittel-fur-endometriose.html, [retrieved on Apr. 20, 2017], 4 pages.
International Search Report (PCT/ISA/210) issued in PCT/IB2017/054667, dated Nov. 3, 2017.
Ososki et al., "Ethnobotanical literature survey of medicinal plants in the Dominican Republic used for women's health conditions", Elsevier. Journal of Ethnopharmacology, vol. 79, No. 3, 2002, pp. 285-298.
Rezazad et al., "Protective effect of Petroselinum crispum extract in abortion using prostadin-induced renal dysfunction in female rats", Avicenna Journal of Phytomedicine (AJP), vol. 4, No. 5, Sep.-Oct. 2014, pp. 312-319.
Written Opinion (PCT/ISA/237) issued in PCT/IB2017/054667, dated Nov. 3, 2017.

* cited by examiner

*Primary Examiner* — Susan Hoffman
(74) *Attorney, Agent, or Firm* — Birch, Stewart, Kolasch & Birch, LLP

(57) ABSTRACT

A medicament includes a parsley extract for use in the treatment and/or prevention of endometriosis. The medicament may also include an oleander extract.

19 Claims, No Drawings

MEDICAMENT FOR THE TREATMENT AND/OR PREVENTION OF ENDOMETRIOSIS

FIELD OF APPLICATION

The present invention generally relates to a medicament for the treatment and/or prevention of endometriosis.

In particular, the invention concerns a medicament based on a parsley extract (*Petroselinum crispum*) for the treatment and/or prevention of endometriosis.

PRIOR ART

Endometriosis is an often painful chronic disease, characterized by the presence of tissue morphologically and biologically similar to the normal endometrium in areas outside of the uterus.

The most common symptom is pain during the menstrual period but it may also occur at other times, especially during sexual intercourse, ovulation, etc.

In addition, endometriosis has a deleterious effect on the ovarian and tubular function and on uterine receptivity, and is therefore one of the major causes of infertility in women.

The pathology has invalidating consequences, both in terms of health and work, by altering the quality of life of affected women, affecting their relationships, family relations, at work, and reproductive abilities.

In Europe, endometriosis affects about 10% of women in reproductive age with prevalence among women aged 30 to 40 years and it manifests itself with pain in about 75% of the cases, 25% of the cases being of the asymptomatic type.

The purpose of endometriosis therapy includes symptom relief, endometrial foci resolution and the prevention of new endometrial tissue ectopic foci and the restoration of reproductive capacity.

Current therapeutic approaches are however far from being curative and focus on combinations of medical, surgical and psychological therapies.

The benefits of these joint therapies have not been demonstrated, particularly in improving the quality of life and the expectations that women have for their lives.

In addition, although it is at least theoretically advantageous, there is no evidence that a surgical medical combination treatment of endometriosis increases the fertility rate, but instead it unnecessarily delays the reproductive age of the patients.

Surgical and hormonal treatment of endometriosis ultimately results in severe side effects and a high incidence of relapse. From 55% to 100% of women develop adhesions after pelvic surgery, which in turn can cause infertility, chronic abdominal and pelvic pain and make it difficult to perform further surgery.

The intensity of the pain perceived by women is weakly correlated to the extension of the endometriosis or its stage (from 1 to 4, according to the classification of the *American Society for Reproductive Medicine*), with some women experiencing very little pain despite having extensive endometrial lesions while others experience severe pain despite being in the presence of small endometrial spots.

At present, there is no definitive endometriosis therapy and the most common treatments are: analgesic therapy, hormone therapy, and surgical therapy.

The analgesic pain therapy can be helpful in the case where the pain is moderate. Drugs used in this pathology range from OTC analgesics to morphine derivatives.

Usually, non-steroidal anti-inflammatory drugs (NSAIDs) and opioids are used in this context, which are very powerful but which provoke known undesirable interactions with the nervous system.

Unfortunately, it has been shown that the efficacy of analgesics in alleviating the pain associated with endometriosis is definitely limited.

As for hormone therapy, since ovarian hormones cause a menstrual cycle in the endometrial cells and a cycle similar to the menstrual cycle in endometriotic cells, it was decided to use the ovarian hormone production suppression therapy to treat the symptoms of endometriosis.

In other words, the hormone therapy used is aimed at blocking ovarian hormone production, it prevents menstruation and this slows down the growth and the activity of the endometrial cells and consequently of the endometrial lesions.

Hormone therapy could even help prevent the growth of new areas and of new endometrial adhesions but it cannot eliminate existing endometrial lesions.

Generally, one of the following hormonal therapies is prescribed:

1. Oral Contraceptives

With oral contraceptives, pain reduction is temporary, being effective only while taking the contraceptives themselves when the menstrual cycle is suppressed. The symptoms of endometriosis return with the interruption of the treatment.

Many women continue the treatment indefinitely and this delays their eventual fertility.

Moreover, many women continue to have pelvic pain even while taking the hormone contraceptive.

It is also worth mentioning the side effects of contraceptives such as weight gain, intermenstrual spotting (especially when women take the contraceptive pill without interruption), alteration of the lipid and coagulation profile, etc.

2. Progesterone and Progestins

Taken as pills, in long-term injections or as a Mirena® intrauterine device, progesterone and progestins improve the symptoms by reducing the size of the endometrial lesions and reduce or block the menstrual flow completely (one third of women using a progesterone intrauterine spiral no longer has menstruation after one year of therapy).

This therapy naturally has the disadvantage of preventing a pregnancy. In addition, especially in the first year of therapy, one third of women continues to have bleeding several times a year, and during these episodes of bleeding the pain of endometriosis reappears (proving that these therapies are not curative but only symptomatic).

Sometimes it takes several months before the menstrual cycle resumes after treatment has been suspended.

Women who take these progestin hormones often have symptoms: they may gain weight, feel depressed or have irregular vaginal bleeding, etc.

3. Gonadotropin-Releasing Hormone (GnRH) Agonist

This hormone is even more potent in blocking the production of ovarian sexual hormones by putting the body in a "menopause" state. It prevents ovulation, menstruation and growth of the endometrium—and therefore of endometriosis—without providing a hormone replacement (as in the therapies discussed above), and cannot be taken for more than 6 consecutive months.

GnRH agonists are marketed as nasal sprays or as injections to be taken once a month or once every three months; most doctors recommend a therapy with GnRH agonists for no more than 6 months and with an interim period of several months before repeating the cycle. The risk of cardiac complications and severe osteoporosis is in fact increased if these hormones are taken for more than two years. In addition, it is to be noted that after the suspension of the GnRH agonists, the body exits the 'menopause' state, menstruation resumes, as often does the endometrial pain and any other symptoms of endometriosis.

This therapy with GnRH agonists also has severe side effects such as flushing, tiredness, muscular and articular pain, insomnia problems, headache, depression, osteoporosis and vaginal dryness.

4. Danazol

Danazol blocks the hormonal production of the menstrual cycle. During treatment with Danazol, women have a very irregular menstruation and sometimes they do not have it at all. Very common side effects are increased acne and weight gain, muscle cramps, tiredness, breast tension and breast reduction, headache, dizziness, weakness, flushing and a male tone of the voice.

The side effects of Danazol are more marked than those of the other hormonal therapies and the symptoms of endometriosis resume as soon as the treatment is discontinued.

Danazol may also harm the health of a possible foetus. Since oral contraceptives cannot be taken during Danazol treatment, the use of condoms is recommended to prevent the risk of pregnancy during therapy.

Other hormones in endometriosis therapy are also being studied, such as gestrinone, approved in Europe, and aromatase inhibitors (which reduce the estrogenic level) but which are not approved by the "Food and Drug Administration" for endometriosis therapy.

Finally, regarding surgical therapies, these can sometimes offer significant, but always short-term, relief from the pain of endometriosis, so that sometimes doctors prescribe surgery as a possible option for treating severe endometriosis pain.

The surgery must be carefully planned because it is an irreversible procedure that can even have negative effects on fertility in the case of complications. Currently it is recommended not to operate on endometrial cysts that are smaller than 3 cm and to intervene only in the presence of severe pain.

It should also be remembered that the process that causes endometriosis does not stop with surgery.

Studies show that endometriosis has a relapse of 20%-40% during the 5 years following a conservative surgery.

Therefore, at present, it can be said that endometriosis is a chronic condition that does not have a cure.

This does not mean that efforts are not being made to reduce its impact in daily life, and that analgesic, hormonal or surgical therapies do not offer some improvement, even if only transient, with respect to the pain.

The American College of Obstetricians and Gynecologists (ACOG) also reports clinical trials of presacral neurectomy to reduce pain but this procedure does not seem to have an effect on the pain of endometriosis and is not included in the recommendations for the management of endometriosis by ACOG.

The origin of endometriosis is unknown. However, observations of an increased risk of endometriosis in adolescents with cervical obstruction but with open Fallopian tubes seem to indicate that at least in children or young adolescents a retrograde menstrual flow may occur immediately after birth. Adult stem cells seem responsible for the capacity of the endometrium to regenerate itself and these same cells could be found in the retrograde menstrual flow and cause endometriosis lesions outside the uterus.

Speculations aside, however, it is now certain that endometriosis is one of the major causes of infertility. The mechanisms of infertility remain controversial, including high oxidative stress, an altered immune function, an altered intra-follicular and peritoneal hormonal environment and a reduced uterine receptivity: all of these factors are thought to be responsible for the production of low-quality oocytes, reduced fertilization, and an extremely reduced implantation.

But endometriosis has been found in women who have never suffered from pelvic pain or infertility and it has been found in 20%-25% of asymptomatic women.

Endometriosis in fact is not always the cause of pelvic pain. It has also been observed that pelvic adhesions do not correlate with chronic pelvic pain. Likewise, surgical lysis of adhesions did not alleviate the pain except in very few cases with severe adhesions involving the intestine.

Finally, it has been observed that laparoscopic evaluations in patients experiencing chronic pelvic pain could not be associated to pathological findings in 30-50% of the cases. It has been observed that pathological findings are also present in 30% of healthy subjects who underwent tubal sterilization.

Therefore laparoscopic pathological findings do not necessarily identify the cause of pain and, moreover, as pointed out above, there is no correlation between pain and stages of endometriosis or between the stages of endometriosis and pain or infertility and, vice versa, pelvic pain does not have a univocal association with endometriosis.

The presence of specifically endometrial lesions histologically demonstrated in patients who suffer from pelvic pain is in the order of 15%, while it is of 25% among those who underwent abdominal hysterectomy.

Even in the case of laparoscopy to investigate infertility, the presence of endometriosis was shown in 21% of cases.

On the other hand, as mentioned above, pathological laparoscopic findings of endometrial foci are documented in healthy totally asymptomatic women who underwent laparoscopy for tubular sterilization in about 30% of the cases.

In conclusion, prospective studies show that regardless of the presence of symptoms (sterility, pain, etc.), even when microscopic lesions are considered, 30%-40% of women exhibit endometriosis.

This supports the current idea that endometriosis is, in a large majority of the patients, a paraphysiological condition.

Only in some cases does it become symptomatic, and in this case even minor lesions can cause pain and have implications on the physical well-being and on the reproductive capacity and therefore only in these cases should it be considered an illness.

The presence of peritoneal endometrial lesions during laparoscopy or surgery confirms for various reasons the idea that the incidence of endometrial lesions may not have clinical implications and that the progression of the disease is instead the result of an abnormal cell response (caused by immunological or genetic alterations).

Indeed, cytokines, interleukins, oxidative stress markers, soluble cell adhesion molecules have all been shown to be potential markers in the diagnosis of endometriosis suggesting that the triggering of endometriosis is linked to a change of a toxic nature or in terms of an inflammatory immune response.

Endometriotic cells 'per se' may not be the cause of infertility and pain but rather their reactivity to different external stimuli triggers a pathological response and an inflammatory cascade that is called endometriosis.

Various theories have been put forward to explain the development and progression of endometriosis but for now none combines the various aspects of the disease.

One of the most important findings is the increased expression of several markers (including heat shock protein, fibronectin, and neutrophil elastase) that could be involved in inflammation triggerring processes by stimulation of Toll-Like receptors(TLR).

This would thus create a vicious circle between oxidative stress pathway and that dependent on Toll-Like receptors when the inflammatory process becomes chronic ("danger signal spiral").

Oxidative stress can have an impact on the production of steroid hormones by ovarian granulosa cells, in particular E2 oestrogens, which is an important predictor of ovarian response.

The association between E2 in follicular fluid and total antioxidant capacity suggests that E2 oestrogens may play an important role in the ovarian oxidative balance.

In this regard, experimental data suggest that inflammatory cytokines, in particular the tumor necrosis factor alpha (TNF-alpha), produced by activated macrophages, play an important role in the pathogenesis of endometriosis.

This too tends to favour the theory of a toxic and inflammatory origin of endometriosis.

The detoxification ability can be different in different people and depend on genetic characteristics.

In fact, the evidence of an association between endometriosis and genetic polymorphism is weak. Only carriers of a deletion for the GSTT1 glutathione-S-transferase enzyme, which is a key enzyme in phase II of detoxification, have increased risk of the disease. Studies on genetic expression profiles reveal that the clusters of genes that are most expressed in endometriosis are precisely those of stress and detoxification, confirming the explanation that endometriosis passes from an asymptomatic and paraphysiological state to a state of disease in response to chronic oxidative and inflammation stress, while endometrial tissue has even been observed even in infant females at birth.

It has been observed that prenatal exposure of mice to bisphenol A (BPA), widely used in plastic production and epoxy resins, produces an endometrial type of response in females.

Also the accumulation and transformation of foods genetically modified by pesticides, and the toxicity of some molecules such as glyphosates and Cry1Ab protein, and dioxin-like compounds, seem to play a role in the development of the endometriosic disease.

In a study on 100 women of reproductive age undergoing laparoscopy, the gas chromatography analysis showed that the extremely high presence of six persistent organochlorine pesticides (OCPs), was associated with a five-fold increase in endometriosis with respect to that of the lower tertile. Similar results were observed with t-nonachlor and hexachlorobenzene (HCB) and with dioxin compounds. Conversely, high urinary concentrations of phthalates (phthalates act as an oestrogen disruptor and are a risk factor in oestrogen-dependent diseases) or of cadmium (also acting as a risk factor in oestrogen-dependent diseases) are not associated with an increased risk of endometriosis in infertile women.

This is consistent with the fact that endometriosis is not caused by an endocrine disorder and this is confirmed by the fact that even the eutopic endometrium (i.e., intrauterine) of women with endometriosis has an altered capacity for proliferation and angiogenesis. It seems therefore that the characteristics of the eutopic endometrium determine the fate of the retrograde flow of the endometrial tissue, modulated by a complex network of environmental factors, magnetic fields, diet, sleep pattern, social life, genetic detoxification pattern, toxic substances of chemical origin, liver detoxification system, immune system, infections and chronic inflammatory diseases. Possible factors that can trigger the inflammatory response of endometriotic cells which are known today also according to the Applicant's experience are the following:

Infections, such as chlamydia, mycoplasmas and viruses;

Intoxications, such as from chemicals used on hair (to which hairdressers are principally exposed), glues and solvents, all of which make endometriotic cells reactive.

In these cases, conditions are created for endometriotic cells to become a disease rather than remain silent (as in causal findings during laparoscopy) with effects on pain and fertility.

Eliminating these external stimuli factors may be useful (with known therapies such as antibiotics, antivirals, liver detoxifiers), but it is not enough to deactivate the pathological response signal of endometriotic cells—once it has been created—and return them to their silent state.

In the light of the foregoing, it is even more apparent that the therapies currently in use are not suitable for treating endometriosis and that, instead, in the case where endometriosis is caused by toxic factors, conventional hormone therapies may be even counterproductive inasmuch as they worsen hepatic metabolism making it more difficult for the liver to remove the toxic substances that trigger the inflammatory response of the endometriotic cells.

The technical problem of the present invention is therefore to provide a medicament for the treatment and/or prevention of endometriosis that overcomes the aforementioned drawbacks of the prior art.

Another technical problem of the present invention is to provide such a medicament for the treatment and/or prevention of endometriosis which has a long-term effect, i.e. beyond the period of administration of the medicament.

Another technical problem of the present invention is to provide such a medicament for the treatment of endometriosis that is capable of preventing relapses of endometriosis.

Another technical problem of the present invention is to provide a medicament for the prevention of endometriosis that is able to prevent or delay the onset of endometriosis.

SUMMARY OF THE INVENTION

Such a problem has been solved according to the invention by a medicament comprising a parsley extract for use in the treatment and/or prevention of endometriosis.

Preferably, the parsley extract is an extract of parsley belonging to the *Petroselinum* genus.

Preferably, the parsley extract is an extract chosen from the group consisting of *Petroselinum crispum* extract, *Petroselinum sativum* extract and *Petroselinum segetum* extract, more preferably *Petroselinum crispum* extract.

In other nomenclatures, parsley is also classified as *Carum petroselinum* and *Apium petroselinum*, both of which species are to be considered included in the present invention.

The parsley extract can be of the whole plant or its parts, namely the stalks, (or stems) or the leaves.

Preferably, the parsley extract is an extract of the whole parsley plant (i.e. stems and leaves), more preferably of the fresh parsley plant.

Preferably, the parsley extract is in a form selected from solution, tablet, capsule, and powder, more preferably in the form of a solution.

Preferably, the parsley extract is in the form of a solution and is obtained by extraction in solvent.

Preferably, the parsley extract is obtained by extraction in solvent, wherein the weight ratio between the parsley and the solvent is comprised between 1:15 and 1:3, more preferably comprised between 1:10 and 1:5, even more preferably about 1:10.

Preferably, the solvent is selected from ethyl alcohol, water and mixtures thereof.

When this weight ratio is about 1:10, the extract obtained is a mother tincture.

The parsley extract can be prepared according to methods known in the field.

Preferably, the medicament comprises pharmaceutically acceptable excipients and/or carriers.

Preferably, the medicament is to be administered orally.

Preferably, the medicament is to be administered for an administration period comprised between 20 and 90 days, more preferably comprised between 30 and 70 days.

Preferably the medicament is to be administered daily.

Preferably, the administration period is followed by a further administration period of the medicament comprised between 20 and 90 days, more preferably comprised between 30 and 70 days, more preferably daily.

It has been found in fact that the administration of the medicament for a given administration period, as indicated above, is effective in the treatment of one or more symptoms of endometriosis. In some cases, it may happen that while some symptoms are treated successfully, others persist. It has been observed that in these cases the repetition of the medicament administration for a further administration period as indicated above is useful in the treatment of the remaining symptoms. For the complete resolution of the symptoms, in fact, it is sometimes necessary to repeat the administration.

Preferably, the medicament comprises the parsley extract in the form of a mother tincture and is to be administered in a dosage comprised between 10 and 30 drops per day, more preferably comprised between 10 and 20 drops per day of the parsley extract for an administration period comprised between 20 and 90 days, more preferably comprised between 30 and 70 days.

In an embodiment, the medicament comprises parsley extract in the form of a mother tincture and is to be administered in a dosage comprised between 10 and 30 drops once a day, preferably comprised between 10 and 20 drops once a day of the parsley extract for an administration period comprised between 20 and 90 days, preferably comprised between 30 and 70 days.

In an alternative embodiment, the medicament comprises parsley extract in the form of a mother tincture and is to be administered in a dosage comprised between 5 and 15 drops twice a day, more preferably comprised between 5 and 10 drops twice a day of the parsley extract for an administration period comprised between 20 and 90 days, preferably comprised between 30 and 70 days.

In one embodiment, the treatment and/or prevention of endometriosis comprise the administration of the medicament comprising the parsley extract, preferably in the form of mother tincture, in which the parsley extract is the only active ingredient.

Preferably, the medicament further comprises an oleander extract.

Preferably, the oleander extract is an oleander extract belonging to the *Nerium* genus.

Preferably, the oleander extract is an extract chosen from the group consisting of *Nerium oleander* extract and *Nerium indicum* extract (also known as Indian Oleander), more preferably *Nerium oleander* extract.

Preferably, the oleander extract is an extract of oleander leaves, more preferably fresh oleander leaves.

Preferably, the medicament comprises oleander extract in a non-toxic concentration.

It has been found in fact that the oleander extract exerts an effect of enhancing the parsley extract action, that is, it increases the overall efficacy of the treatment and/or prevention, even when the administration is sequential. This effect has been observed to be particularly marked in smoking patients.

*Nerium oleander* extract is known for its properties as antibacterial, antifungal, anti-HIV, anti-herpes, anti-malaria, analgesic, anti-inflammatory, and for its capacity as neuroprotective cardiac stimulant. Itas antioxidant, anti-angiogenesis, and antitumor capabilities are also recognized (also in humans, where a phase II study of the US Food and Drug Administration (FDA) is underway). Oleander has instead never been proposed for the treatment of endometriosis.

Oleander-based formulations for therapeutic applications have been available for decades in the form of homeopathic solutions and studies show that toxicity in the doses used is null.

Preferably, the oleander extract is in a form selected from solution, tablet and globules, more preferably in the form of a solution.

Preferably, the oleander extract is in the form of a solution and is obtained by extraction in solvent and further dilution in solvent of the intermediate extract thus obtained thus obtaining a decimal dilution comprised between 4 and 60 DH, more preferably comprised between 4 and 6 DH (Hahnemannian dilution).

A decimal dilution value of oleander extract lower than 4 DH (corresponding to a 1:10000 dilution of the extract compared to the solution) is not recommended as it would be toxic. Dilution values above 60 DH could instead yield a product that is too diluted, which would not be effective.

The expression "decimal dilution" means herein the dilution of a substance in a solvent in volumetric ratio between the solute and the solution of 1:10 followed by a dynamization phase according to known technique.

The oleander extract can be prepared according to methods known in the field.

Preferably, the medicament is in a pharmaceutical form for oral administration comprising the parsley extract, more preferably in the form of a mother tincture, and the oleander extract, more preferably in a decimal dilution comprised between 4 and 6 DH, for simultaneous, separate or sequential use, for the treatment and/or prevention of endometriosis.

Preferably, the medicament comprises the parsley extract, more preferably in the form of a mother tincture, and the oleander extract, more preferably in a decimal dilution comprised between 4 and 6 DH, in a weight ratio between the parsley extract and the oleander extract comprised between 6:1 and 1:1, more preferably comprised between 3:1 and 2:1, even more preferably of 2:1.

In one embodiment, the treatment and/or prevention of endometriosis comprises the administration of the parsley extract, preferably in the form of a mother tincture, and the oleander extract in a decimal dilution comprised between 4 and 6 DH in the form of a fixed dose combination.

Preferably, the medicament is in the form of a composition for oral administration comprising a mixture of the parsley extract, more preferably in the form of a mother tincture, and the oleander extract, more preferably in a decimal dilution comprised between 4 and 6 DH.

In an alternative embodiment, the treatment and/or prevention of endometriosis comprise the administration of the parsley extract followed or preceded in sequence by the oleander extract.

Preferably, the treatment and/or prevention of endometriosis comprises an administration period of the parsley extract followed or preceded by an administration period of the oleander extract.

Preferably, the medicament comprises the parsley extract in the form of a mother tincture and the oleander extract in a decimal dilution comprised between 4 and 6 DH and is to be administered in a dosage comprised between 10 and 30 drops per day, more preferably comprised between 10 and 20 drops per day of the parsley extract and in a dosage comprised between 5 and 10 drops per day, more preferably 5 or 6 drops per day of the oleander extract for an administration period comprised between 20 and 90 days, more preferably between 30 and 70 days.

In a preferred embodiment, the medicament comprises the parsley extract in the form of a mother tincture and the oleander extract in a decimal dilution comprised between 4 and 6 DH and is to be administered in a dosage comprised between 10 and 30 drops once a day, more preferably comprised between 10 and 20 drops once a day of the parsley extract, and in a dosage comprised between 5 and 10 drops once a day, more preferably 5 or 6 drops once a day of the oleander extract for an administration period comprised between 20 and 90 days, more preferably between 30 and 70 days.

In an alternative embodiment, the medicament comprises the parsley extract in the form of a mother tincture and the oleander extract in a decimal dilution comprised between 4 and 6 DH and is to be administered in a dosage comprised between 5 and 15 drops twice a day, more preferably comprised between 5 and 10 drops twice a day of the parsley extract and in a dosage comprised between 3 and 5 drops twice a day, more preferably oleander extract 2 or 3 drops twice a day of the oleander extract for an administration period comprised between 20 and 90 days, more preferably comprised between 30 and 70 days.

Preferably, the medicament is to be administered to patients in which endometriosis occurs with one or more symptoms among: chronic pelvic pain, especially during the menstrual cycle, intermenstrual ovarian pain, evacuation pain, infertility, dyspareunia, more preferably chronic pelvic pain, especially during the menstrual cycle, intermenstrual ovarian pain, evacuation pain and infertility.

In a preferred embodiment, the treatment of endometriosis comprises a pre-treatment with one or more agents among anti-inflammatory agents, hepatic and/or renal and/or intestinal drainage agents, antibiotic agents, antimycoplasm agents, antichlamydia agents, antifungal agents and antiviral agents.

Preferably, the medicament is to be administered to patients who, following a diagnosis of endometriosis, have previously undergone one or more pre-treatments with one or more agents chosen from anti-inflammatory, hepatic and/or renal and/or intestinal drainage, antibiotic, anti-mycoplasm, antichlamydia, antifungal, and antiviral agents to remove the triggering cause of the inflammatory response of the endometriotic cells.

The present invention also relates to a kit of parts comprising: a) the abovesaid parsley extract and (b) the abovesaid oleander extract for the treatment and/or the prevention of endometriosis. The expression "kit of parts" refers to a preparation comprising as active ingredients the abovesaid parsley extract and the abovesaid oleander extract for the simultaneous, separate or sequential use for the treatment and/or prevention of endometriosis.

The present invention also relates to a method for the treatment of endometriosis comprising administering the medicament or kit of the invention to patients in need thereof.

Surprisingly in fact it has been found that, unlike patients undergoing the therapies of the prior art, which do not prevent relapse of endometriosis symptoms at the end of the therapy itself, most patients with pain and/or infertility associated to endometriosis and which have been treated with the medicament of the present invention report a considerable improvement or the total disappearance of one or more symptoms, sometimes of all the symptoms, and the absence of relapse of symptoms even after periods of years after therapy. In some patients, the occurrence of spontaneous pregnancies even repeated has also been observed without the need to undergo treatment again.

Without wishing to be bound by any theory, it is hypothesized that the medicament of the present invention is effective in restoring and maintaining the endometrial tissue in a quiescent state.

It has also been observed that the medicament of the present invention is particularly effective in cases where patients had previously undergone one or more pre-treatments with one or more agents among anti-inflammatory, hepatic and/or renal agents and/or intestinal drainage, antibiotic, anti-mycoplasm, antichlamydia, antifungal and antiviral agents, prior to its administration.

As explained above, in fact, the symptoms of endometriosis can occur in subjects who would have remained asymptomatic had they not come into contact with external triggers such as toxins, bacteria, viruses, etc., against which their reaction capacity was ineffective, causing an activation (i.e. inflammation) of the endometrial tissue, leading to the known painful symptoms and/or infertility.

Once the patient has been treated, following diagnosis, for the elimination of the triggering cause, the administration of the medicament of the present invention gives the patient complete remission from the disease, total resolution of the symptoms, rapid recovery of fertility, the restoration of the normal endometrial function (both eutopic and ectopic), and less likelihood of relapses.

In particular, it has been observed that the medicament of the present invention allows to achieve a considerable improvement in one or more or all of the symptoms of endometriosis, more particularly chronic pelvic pain, especially during the menstrual cycle, intermenstrual ovarian pain, infertility and dyspareunia. It has been observed in fact that the painful phenomena caused by endometriosis can disappear completely following treatment with the medicament of the present invention (including dysmenorrhea and dyspareunia) and that considerable improvements in fertility can be obtained.

According to the same principle, the medicament of the present invention also allows to prevent the onset of endometriosis symptoms in subjects with asymptomatic endometriosis.

It has also been noted that the medicament of the present invention does not cause any side effects and is instead well tolerated by patients.

DETAILED DESCRIPTION OF THE INVENTION

The invention will now be further described with reference to embodiments provided for illustrative and non-limiting purposes.

Example 1

Case 1

A 25-year-old patient who had previously had an extra-uterine pregnancy with removal of the left Fallopian tube, was examined. She had also undergone laparoscopy for dysmenorrhoea and desired pregnancy and had received a diagnosis of large endometrial adhesions and foci. The patient complained of great menstrual pain unchanged after laparoscopy and sought infertility counselling as she wanted to have children but was unable.

The patient first underwent an azithromycin-based pre-treatment against Chlamydial infections and a Bufo-(FMS Bufo Complex, distributed by Omeopiacenza S.r.l.) and Crotalus-based pre-treatment (FMS Crotalus Complex, distributed by Omeopiacenza S.r.l.), the latter two agents acting as antiviral agents to counter these suspect infections.

Subsequently, the patient was treated with a parsley mother tincture (ethyl alcohol solvent) with a dose of 10 drops in the morning and 10 drops in the evening, every day for two months.

At the end of the therapy, the patient no longer complained of pain. However, she had not been able to get pregnant.

The above parsley mother tincture therapy was thus repeated for a further two months.

At the end of the second cycle, the patient was pregnant but had a miscarriage at the fifth week. About a month and a half later the patient became spontaneously pregnant again and gave birth to a healthy child.

The patient reports that she has had no longer had any endometrial pain and had not noticed any side effects associated to the treatment.

Example 2

Case 2

A 31-year-old patient was examined who had had an extra-uterine pregnancy eleven years earlier; she had also undergone laparoscopic surgery two years before that for endometriosis which had confirmed the endometriosis condition and blockage of the right Fallopian tube. Many adhesions were present. The patient complained of severe pain during menstruation.

The patient underwent pre-treatment against mycoplasmas with azithromycin and non-steroidal anti-inflammatory drugs based on the diagnosis at the time of the examination.

Subsequently, the patient underwent therapy with a parsley mother tincture (ethyl alcohol solvent) with a dose of 10 drops in the morning and 10 drops in the evening, every day for two months.

The patient reports that she had not noticed any side effects associated to the treatment.

At the end of treatment, the patient became pregnant and had a spontaneous labour at the eighth month.

After pregnancy, the endometrial cyst was observed to be 48 mm×41 mm and the patient complained of pain again, though less intense than that prior to treatment.

The patient underwent again the parsley mother tincture therapy and at the end of the two months the pain had gone.

Example 3

Case 3

A 33-year-old patient was examined who had endometrial cysts of 3 cm and who for about two years had been undergoing continuous oral contraceptive therapy for endometriosis-related pain. She had recently interrupted therapy because she wanted to have children.

The patient underwent pre-treatment with hepatic and antiviral drainage agents (FMS Bufo Complex, distributed by Omeopiacenza S.r.l. and FMS Crotalus Complex, distributed by Omeopiacenza S.r.l.), based on the diagnosis at the time of the examination, and was subsequently treated with a parsley mother tincture (ethyl alcohol solvent) with 10 drops in the morning and 10 drops in the evening, every day for two months and with an oleander extract 6 DH dilution, at the dosage of 5 drops in the morning every day for two months.

After two months, the patient was pregnant spontaneously and had a full-term labour. After delivery, a 45 mm endometrial cyst was observed but no symptoms.

The patient reports that she had not noticed any side effects associated to the treatment.

Example 4

Case 4

A 41-year-old patient was visited, who had diagnosis of endometriosis, complaining of very severe pelvic, menstrual and rectal pain, dyspareunia and infertility.

The diagnosis indicated a 3 cm endometrial ovarian cyst and a endometrial nodule in the Pouch of Douglas: previously treated with oral contraceptives, then with Livial, Enantone, and even GnRh analogues to reduce the pain of the endometriosis without much success. The patient wanted to have children.

The patient underwent pre-treatment based on antiviral agents (FMS Bufo Complex produced by Omeopiacenza S.r.l. and FMS Crotalus Complex produced by Omeopiacenza S.r.l.) and also a hepatic drainage agent (*Carduus marianus* mother tincture) based on the diagnosis at the time of the examination.

The patient was treated with a parsley mother tincture (ethyl alcohol solvent) with a dosage of 10 drops in the morning and 10 drops in the evening, every day, for two months. She got pregnant in the third month of therapy, her pregnancy is still in progress and she has now reached the $7^{th}$ month without complications.

The patient reports that she no longer has painful symptoms and has not noticed any side effects associated to the treatment.

The invention claimed is:
1. A method for treating endometriosis comprising administering a medicament to a patient in need thereof;
   wherein the medicament comprises a parsley extract for use in the treatment and/or prevention of endometriosis.
2. The method according to claim 1, wherein said parsley extract is an extract chosen from the group consisting of *Petroselinum crispum* extract, *Petroselinum sativum* extract and *Petroselinum segetum* extract.

3. The method according to claim 1, wherein said parsley extract is an extract of the whole parsley plant.

4. The method according to claim 1, wherein said parsley extract is in a form chosen from solution, tablet, capsule, and powder.

5. The method according to claim 1, wherein the medicament is administered orally.

6. The method according to claim 1, wherein the medicament is administered for an administration period comprised between 20 and 90 days.

7. The method according to claim 6, wherein said administration period is followed by a further administration period of the medicament comprised between 20 and 90 days.

8. The method according to claim 3, wherein the medicament comprises said parsley extract in the form of a mother tincture and is administered in dosage comprised between 10 and 30 drops per day of said parsley extract for an administration period comprised between 20 and 90 days.

9. The method according to claim 8, wherein the medicament is administered in dosage comprised between 5 and 15 drops twice a day of said parsley extract for an administration period comprised between 20 and 90 days.

10. The method according to claim 1, wherein the medicament further comprises an oleander extract.

11. The method according to claim 10, wherein said oleander extract is an extract chosen from the group consisting of *Nerium oleander* extract and *Nerium indicum* extract.

12. The method according to claim 10, wherein said oleander extract is an extract of oleander leaves.

13. The method according to claim 10, wherein said oleander extract is in a form chosen from solution, tablet, and globules.

14. The method according to claim 13, wherein said oleander extract is in the form of a solution and is obtained by extraction in solvent and further dilution in solvent of the intermediate extract thus obtained thus obtaining a decimal dilution comprised between 4 and 60 DH (Hahnemannian dilution).

15. The method according to claim 10, wherein the medicament is in a pharmaceutical form for oral administration comprising said parsley extract, and said oleander extract, for simultaneous, separate or sequential use, for the treatment and/or the prevention of endometriosis.

16. The method according to claim 10, wherein the medicament comprises said parsley extract and said oleander extract, in a weight ratio between said parsley extract and said oleander extract comprised between 6:1 and 1:1.

17. The method according to claim 10, wherein the medicament comprises said parsley extract in the form of a mother tincture and said oleander extract in a decimal dilution comprised between 4 and 6 DH and is administered in a dosage comprised between 10 and 30 drops per day of said parsley extract and in a dosage comprised between 5 and 10 drops per day of said oleander extract for an administration period comprised between 20 and 90 days.

18. The method according to claim 17, wherein the medicament is administered in a dosage comprised between 5 and 15 drops twice a day of said parsley extract and in a dosage comprised between 3 and 5 drops twice a day of said oleander extract for an administration period comprised between 20 and 90 days.

19. The method according to claim 1, wherein the medicament is administered to a patient that has previously undergone, following a diagnosis of endometriosis, one or more pre-treatments with one or more agents selected from the group consisting of anti-inflammatory agent, hepatic drainage agent, renal drainage agent, intestinal drainage agent, antibiotic agent, antimycoplasm agent, antichlamydia agent, antifungal agent and antiviral agent to remove the triggering cause of the inflammatory reaction of the endometriotic cells.

* * * * *